(12) United States Patent
Tuijthof et al.

(10) Patent No.: US 10,660,662 B2
(45) Date of Patent: May 26, 2020

(54) SURGICAL DEVICE, IN PARTICULAR FOR MINIMALLY INVASIVE SURGERY

(71) Applicant: Technische Universiteit Delft, Delft (NL)

(72) Inventors: Gabriëlle Josephine Maria Tuijthof, Delft (NL); Tim Horeman, Delft (NL)

(73) Assignee: Technische Universiteit Delft, Delft (NL)

( * ) Notice: Subject to any disclaimer, the term of this patent is extended or adjusted under 35 U.S.C. 154(b) by 407 days.

(21) Appl. No.: 15/541,808

(22) PCT Filed: Jan. 5, 2016

(86) PCT No.: PCT/NL2016/050004
§ 371 (c)(1),
(2) Date: Jul. 13, 2017

(87) PCT Pub. No.: WO2016/111621
PCT Pub. Date: Jul. 14, 2016

(65) Prior Publication Data
US 2018/0092656 A1    Apr. 5, 2018

(30) Foreign Application Priority Data
Jan. 6, 2015 (NL) .................................. 2014087

(51) Int. Cl.
*A61B 17/29* (2006.01)
*A61B 17/00* (2006.01)
*A61B 90/00* (2016.01)

(52) U.S. Cl.
CPC ...... *A61B 17/29* (2013.01); *A61B 2017/0046* (2013.01); *A61B 2017/00327* (2013.01);
(Continued)

(58) Field of Classification Search
CPC ......... A61B 17/29–295; A61B 17/068–07292; A61B 17/0469–0483; A61B 17/00234;
(Continued)

(56) References Cited

U.S. PATENT DOCUMENTS

| | | | |
|---|---|---|---|
| 5,792,165 A | * | 8/1998 | Klieman ............... A61B 17/29 606/170 |
| 5,865,361 A | | 2/1999 | Milliman et al. |

(Continued)

FOREIGN PATENT DOCUMENTS

| | | |
|---|---|---|
| EP | 2100562 | 9/2009 |
| EP | 2412319 | 2/2012 |

(Continued)

OTHER PUBLICATIONS

International Search Report and the Written Opinion Dated Jul. 11, 2016 From the International Searching Authority Re. Application No. PCT/NL2016/050004. (12 Pages).

*Primary Examiner* — Jonathan A Hollm

(57) ABSTRACT

Surgical device having a shaft with a distal end including a surgical instrument, and a proximal end including an actuation device; wherein the surgical instrument is mounted on sliders longitudinally movable in opposite directions relative to each other in the shaft by operation of the actuation device, the sliders provided adjacent to each other within the shaft; wherein in a first mounted position the sliders are coupled with the actuation device and are secured against rotation within the shaft to prevent releasing of the coupling between the sliders and the actuation device, and in a second dismountable position the sliders are concurrently slidable at least partly out of the shaft to a point at which rotation of the remainder of the sliders within the shaft is enabled, and the coupling between the sliders and the actuation device is releasable.

13 Claims, 8 Drawing Sheets

(52) U.S. Cl.
CPC .............. *A61B 2017/2916* (2013.01); *A61B 2017/2927* (2013.01); *A61B 2090/0813* (2016.02)

(58) Field of Classification Search
CPC ..................... A61B 2017/2901–2948; A61B 2017/0688–07285; A61B 2017/047–048; A61B 2017/00238–00362; A61B 18/00; A61B 18/1442–1447; A61B 2018/145–1462; A61B 2018/00571–0063; A61B 2018/0091–00958
See application file for complete search history.

(56) References Cited

U.S. PATENT DOCUMENTS

| | | | | |
|---|---|---|---|---|
| 2007/0084898 | A1* | 4/2007 | Scirica | A61B 17/0684 227/176.1 |
| 2008/0021278 | A1* | 1/2008 | Leonard | A61B 17/1608 600/129 |
| 2010/0010512 | A1* | 1/2010 | Taylor | A61B 17/04 606/144 |

FOREIGN PATENT DOCUMENTS

| | | |
|---|---|---|
| EP | 2676615 | 12/2013 |
| WO | WO 99/15090 | 4/1999 |

\* cited by examiner

SURGICAL DEVICE, IN PARTICULAR FOR MINIMALLY INVASIVE SURGERY

RELATED APPLICATIONS

This application is a National Phase of PCT Patent Application No. PCT/NL2016/050004 having International filing date of Jan. 5, 2016, which claims the benefit of priority of Netherlands Patent Application No. 2014087 filed on Jan. 6, 2015. The contents of the above applications are all incorporated by reference as if fully set forth herein in their entirety.

FIELD AND BACKGROUND OF THE INVENTION

The invention relates to a surgical device, in particular for minimally invasive surgery, having a shaft with a distal end equipped with a surgical instrument, for instance a grasper, and a proximal end equipped with an actuation device for the surgical instrument, and wherein the surgical instrument is mounted on sliders that are longitudinally movable in opposite directions with respect to each other in the said shaft by operation of the said actuation device for actuating the surgical instrument, which sliders are provided adjacent to each other within said shaft.

Such a surgical device is known from WO2014148898. In this known device the actuation device is coupled with a handgrip, but within the scope of this invention it is also envisaged that the actuation device can be coupled with other mechanical actuation means which do not form part of a handgrip.

Despite all the merits of the known device, it does not yet provide an explicit solution for the problem how to arrange that the surgical device is at the same time secure and reliable in its integrity of construction during its intended use, and yet provide that the surgical device is dismountable in its component parts so as to enable that it can effectively be cleaned and sterilized after its intended use.

SUMMARY OF THE INVENTION

It is an object of the invention to provide such an explicit solution for this problem as meant in the previous paragraph.

It is also an object of the invention to provide the surgical device according to the preamble which can easily be cleaned and sterilized and thus be repetitively reused.

It is still another object of the invention to provide a surgical device according to the preamble, with correspondingly reduced costs of use.

EP-A-2 100 562 discloses a surgical device according to the preamble of claim 1, wherein the sliders comprise a first mounted position and a second dismountable position, and wherein in the first mounted position the sliders are coupled with a bayonet coupling with the actuation device and are secured while in this first mounted position against rotation within the said shaft, to prevent releasing of the bayonet coupling between the sliders and the actuation device, and that in the second dismountable position the sliders are concurrently slidable at least partly out of said shaft to a point at which rotation of the remainder of the sliders within the said shaft is enabled, and the bayonet coupling between the sliders and the actuation device is releasable.

The surgical device of the invention has the features of one or more of the appended claims.

In a first aspect of the invention the surgical device is in accordance with the main claim arranged such that the actuation device comprises an actuation wheel for the sliders mounted around and at the proximal end of the shaft, which actuation wheel is equipped with transfer means that are coupled to the sliders to convert rotational motion of said actuation wheel into longitudinal yet opposite motions of the sliders, and that a locking plate is provided which is movable between a first position in which it restricts movement of the actuation wheel along the shaft in its longitudinal direction, and a second position in which it enables movement of the actuation wheel along the shaft in its longitudinal direction, and that the transfer means of the actuation wheel are embodied with slits in said actuation wheel that cooperate with radially outwards extending first pins mounted on longitudinally movable inserts that are further equipped with radially inwards extending second pins that reach through longitudinally provided slits in the shaft and eventually into apertures provided in the sliders within said shaft, which radially inwards extending second pins together with said apertures in the sliders embody the said bayonet coupling between the actuation device and the sliders. This arrangement provides effectively that the locking plate secures that in its first position the sliders are maintained in the first mounted position, and further that with the locking plate in its second position the sliders are released to the second dismountable position.

Preferable ways in which the features of the main claim can be implemented are provided in the following disclosure.

In one suitable arrangement the sliders are provided with sidewardly extending pins and the shaft is at its distal end provided with fissures or vice versa, wherein the pins cooperate with the fissures to secure the sliders against rotation within the shaft.

In a further embodiment it is arranged that between the sliders a central rod is provided that has a fixed link with the surgical instrument, and which rod has at its extremity distant from the surgical instrument first locking means that are arranged to cooperate with second locking means provided on a handgrip and/or mechanical actuation means. This provides additional security regarding the constructional integrity of the surgical device during its intended use.

One other beneficiary feature of the surgical device of the invention is that movement of the locking plate from the first position to the second position is linked to releasing the first and the second locking means from each other.

The invention will hereinafter be further elucidated with reference to the drawing of an exemplary embodiment of an apparatus according to the invention that is not limiting as to the appended claims.

BRIEF DESCRIPTION OF THE SEVERAL VIEWS OF THE DRAWINGS

In the drawing.

Whenever in the figures the same reference numerals are applied, these numerals refer to the same parts.

DESCRIPTION OF SPECIFIC EMBODIMENTS OF THE INVENTION

Figure 1:
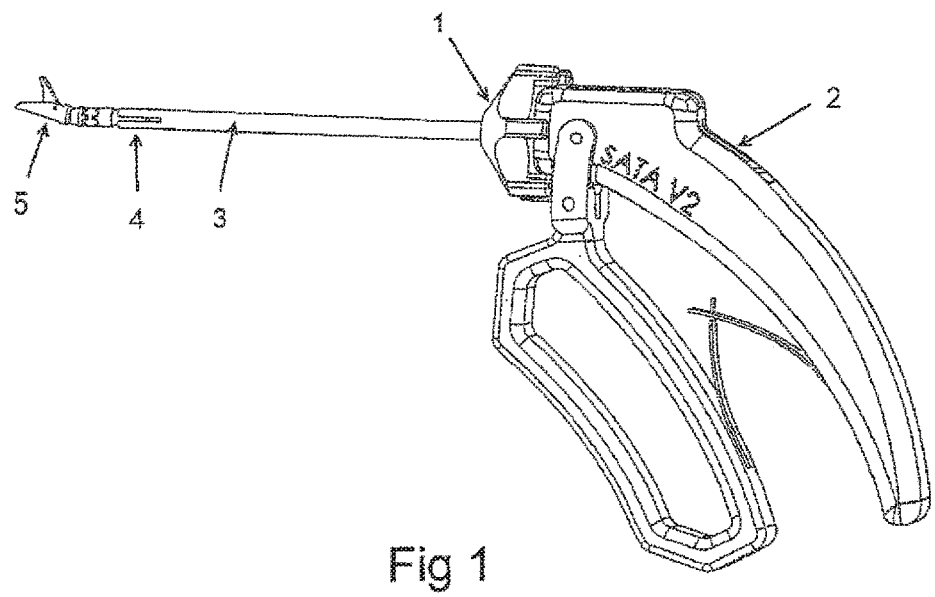
FIG. 1 shows the surgical device of the invention embodied with a handgrip.

Making first reference to FIG. 1 a surgical device 1 is shown which is embodied with a handgrip 2. The invention is however not restricted to this type of surgical device; instead of the handgrip 2 also other mechanical actuation means can be coupled with the surgical device of the invention which may be appropriate depending on the requirements that the user wishes to accomplish.

Figure 2:
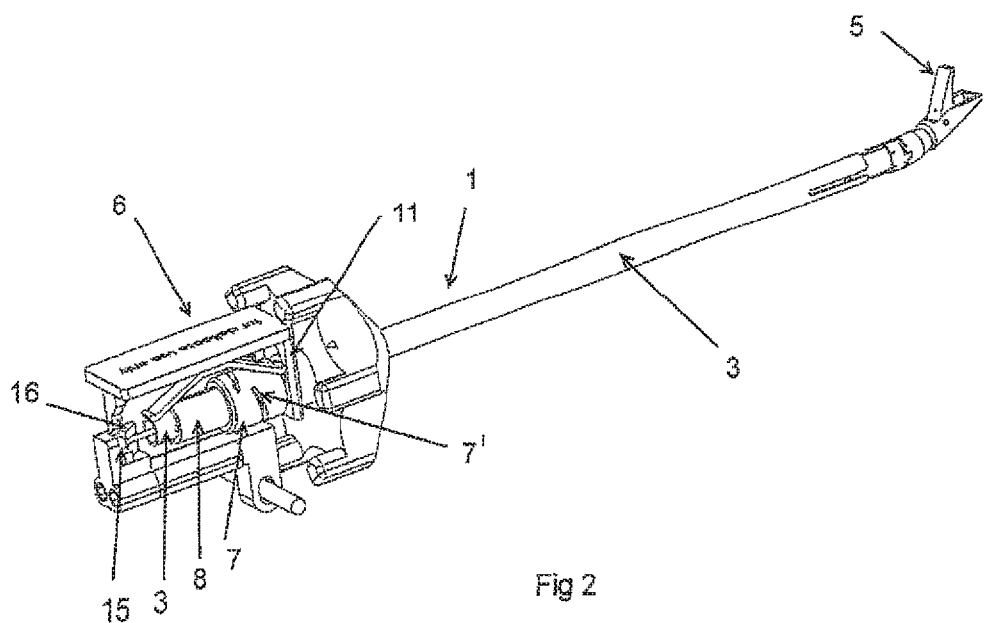
FIG. 2 shows the surgical device of the invention without handgrip or other mechanical actuation means.
Figure 3:
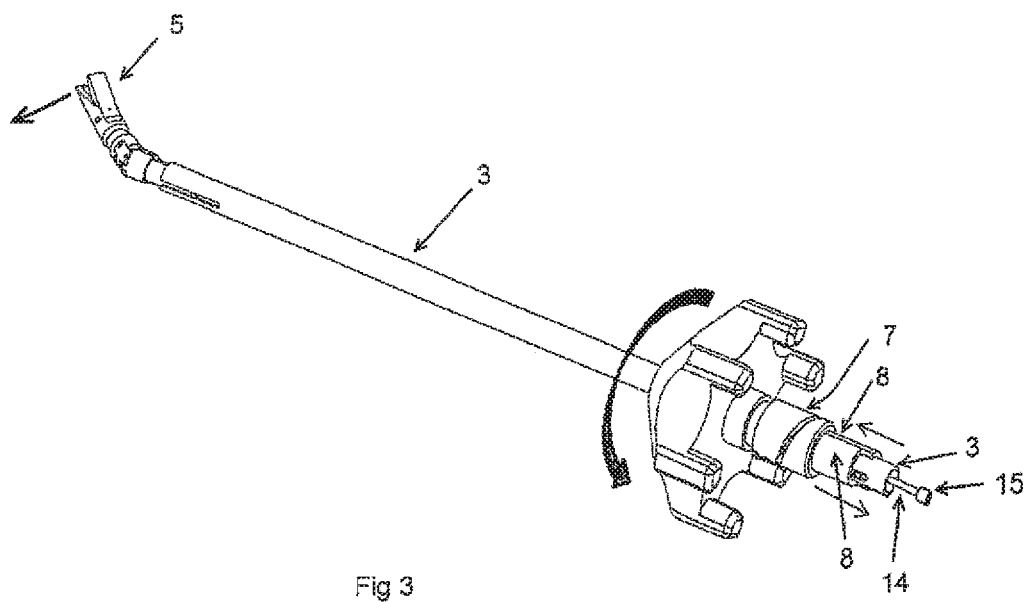
FIG. 3 shows normal operation of the surgical device of the invention when in the locked condition and wherein for clarity certain parts are omitted.

A surgical device 1 as shown in FIG. 1 is typically used in minimally invasive surgery. The surgical device 1 has a shaft 3 with a distal end 4 equipped with a surgical instrument 5, for instance a grasper. In FIG. 2 the surgical device 1 is for clarity shown without handgrip, wherein it can be seen that it has a proximal end 6 where an actuation device 7, 8 for the surgical instrument 5 is provided. This actuation device is further clearly shown in FIGS. 3, 4, and 5. The operation of this actuation device 7, 8 and its function to enable the surgical device of the invention to being switched between the locked position for regular use and the unlocked position for cleaning and sterilization, will become clear in the following.

Figure 6:
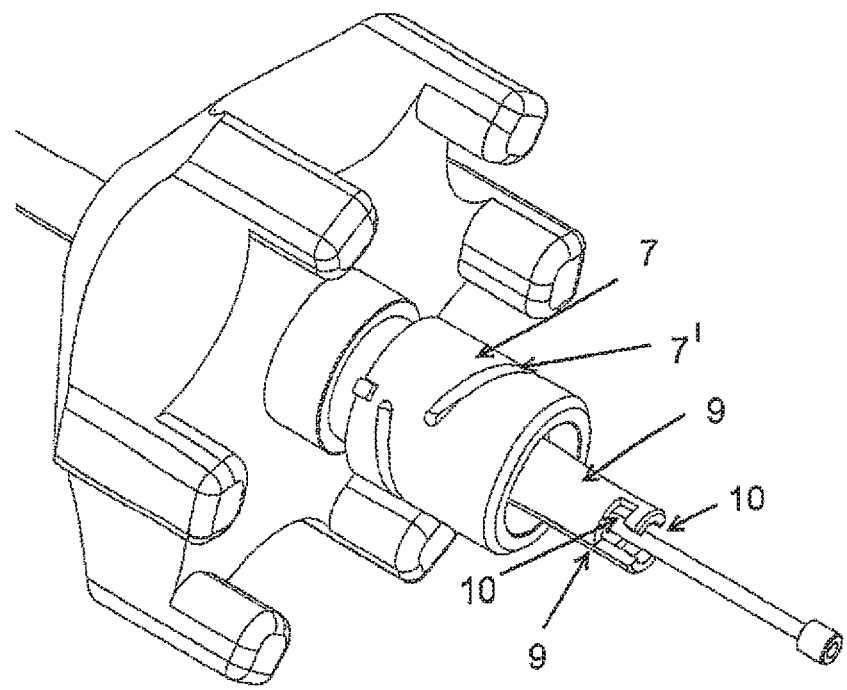
FIG. 6 corresponds to what is shown in FIG. 5, without showing the shaft.

In a manner that is disclosed in the applicant's earlier application WO2014148898, which is deemed inserted herein by reference, the surgical instrument 5 is mounted on sliders that are longitudinally movable in opposite directions with respect to each other in the said shaft 3 by operation of the said actuation device 7, 8 for actuating the surgical instrument 5. These sliders (identified with reference 9 in FIGS. 6 and 8 to be discussed hereafter) are provided adjacent to each other within said shaft 3.

The actuation device 7, 8 comprises an actuation wheel 7 for the sliders 9 mounted around and at the proximal end of the shaft 3. This actuation wheel 7 is equipped with transfer means 7', 8 that are coupled to the sliders 9 to convert rotational motion of said actuation wheel 7 into longitudinal yet opposite motions of the sliders 9 so as to control the surgical instrument 5 during its intended use.

Figure 4:
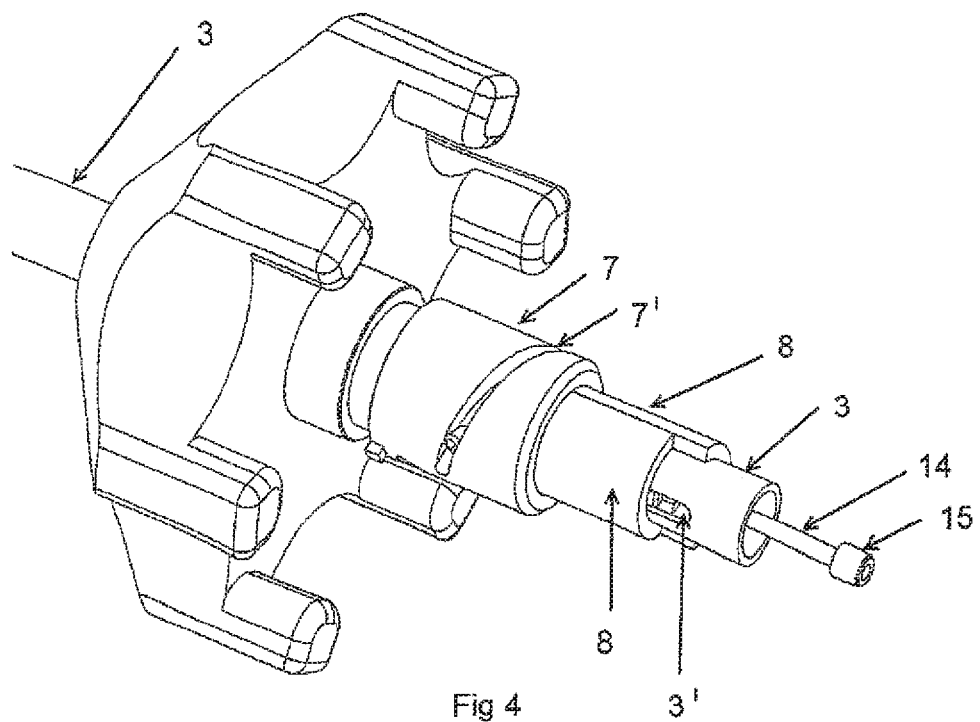
FIG. 4 provides a detailed view of FIG. 3.
Figure 5:
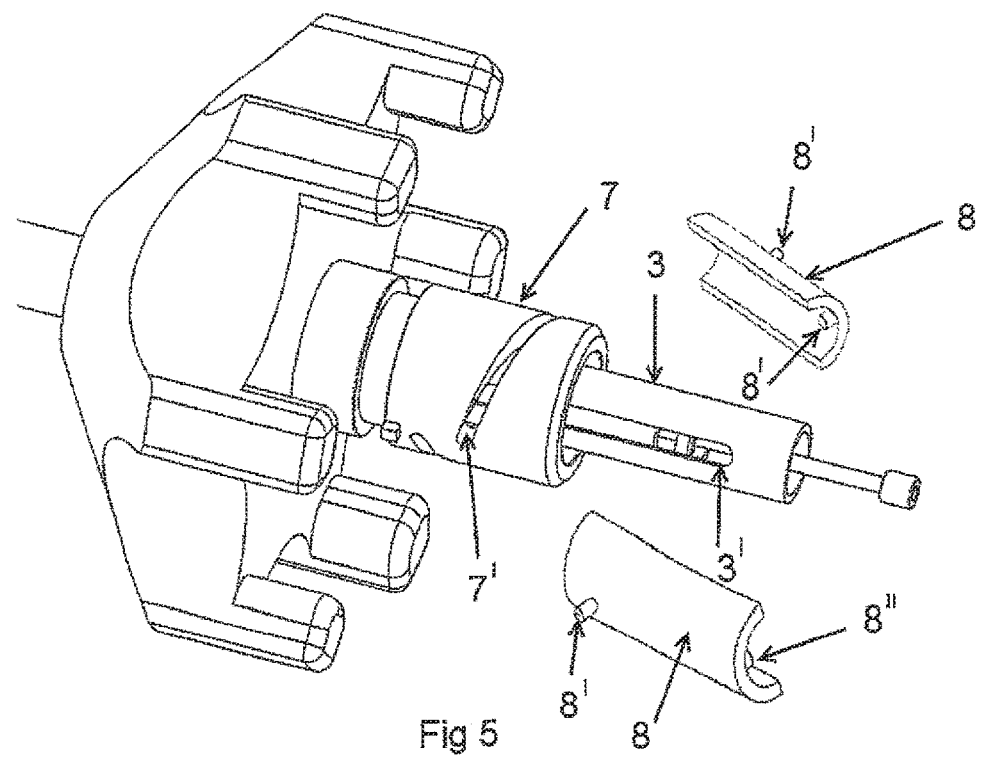
FIG. 5 provides a partly exploded view of FIG. 4.

As may be readily understood from FIG. 4, and in particular from FIG. 5, the transfer means 7', 8 of the actuation wheel 7 are preferably embodied with slits 7' in said actuation wheel 7 that cooperate with radially outwards extending first pins 8' mounted on longitudinally movable inserts 8 that are further equipped with radially inwards extending second pins 8". These second pins 8" reach through longitudinally provided slits 3' in the shaft 3 where they are coupled with the sliders 9 that are housed within the shaft 3. To clarify this, reference is made to FIG. 6 wherein in comparison to FIG. 5 the shaft 3 is not shown so as to provide a direct view on the sliders 9 that are within the shaft 3. For the purpose of coupling the said second pins 8" with the sliders 9, said second pins 8" reach into the apertures 10 provided in the sliders 9, so that these radially inwards extending second pins 8" together with said apertures 10 in the sliders 9 embody the earlier mentioned bayonet coupling between the actuation device 7, 8 and the sliders 9.

An important aspect of the invention is that when the actuation wheel 7 is restricted in movement along the longitudinal direction of the shaft 3, longitudinal movement of the sliders 9 within the shaft 3 is possible but only when they move in opposite directions. A concurrent movement of the sliders 9 in the same direction is not possible, and is only made possible together with and after the actuation wheel 7 is enabled to move along the shaft 3 in its longitudinal direction. In this connection reference is made again to FIG. 2 showing a locking plate 11 placed in its first position in which it restricts movement of the actuation wheel 7 along the shaft 3 in its longitudinal direction. The locking plate 11 can however be moved into a (not shown) second position in which it enables movement of the actuation wheel 7 along the shaft 3 in its longitudinal direction. This is the case in FIG. 7 which represents the situation that the locking plate 11 (not shown) is moved to such a second position. In that situation the sliders 9 can move concurrently in the same direction to a dismountable position.

Figure 7:
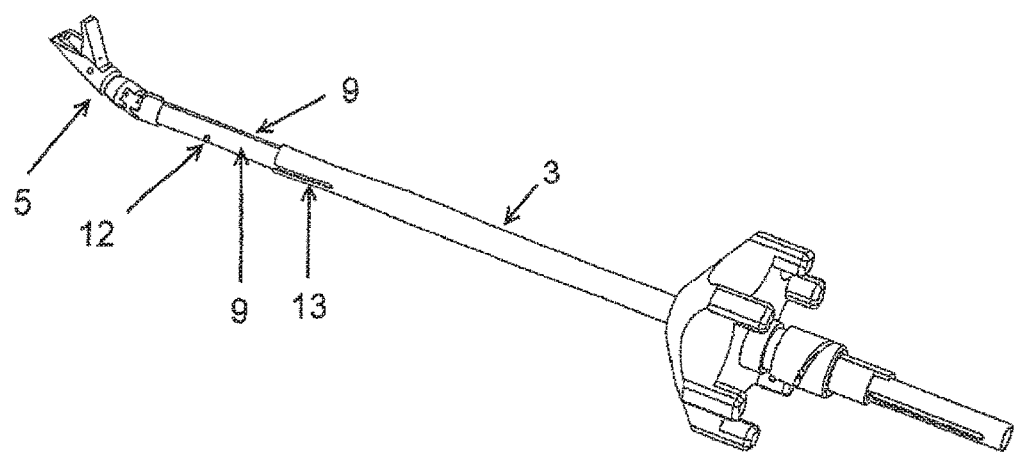
FIG. 7 shows the surgical device of the invention in the unlocked condition.

FIG. 7 shows further that the sliders 9 are provided with sidewardly extending pins 12 and that the shaft 3 is at its distal end provided with fissures 13 (or the other way around with slits in the sliders and pins in the shaft), so that the pins 12 normally cooperate with the fissures 13 to secure the sliders 9 against rotation within the shaft 3. This security against rotation which is required to maintain the bayonet coupling is however lost when the sliders 9 have moved so far that the pins 12 do no longer cooperate with the fissures 13. Then the bayonet coupling between the actuation device 7, 8 and the sliders 9 as embodied by the second pins 8" of the transfer means 8 reaching into the apertures 10 provided in the sliders 9, can be easily released. The sliders 9 thus comprise a first mounted position as shown in FIG. 2 and a second dismountable position as shown in FIG. 7, wherein in the first mounted position (FIG. 2) the sliders 9 are coupled through the earlier mentioned bayonet coupling with the actuation device 7, 8 and are secured against rotation within the said shaft 3 to prevent releasing of the bayonet coupling between the sliders 9 and the actuation device 7, 8. In the second dismountable position (FIG. 7) the sliders 9 are concurrently moved out of said shaft 3 to a point at which rotation of the remainder of the sliders 9 within the said shaft 3 is enabled, and the bayonet coupling between the sliders 9 and the actuation device 7, 8 is releasable. This is all effectively realized by arranging that the locking plate 11 secures that in its first position the sliders 9 are in the first mounted position (FIG. 2) preventing longitudinal movement of the actuation wheel 7 along the shaft 3, and when the locking plate 11 is in its second position (FIG. 7) the sliders 9 are in the second dismountable position, wherein longitudinal movement of the actuation wheel 7 along the shaft 3 is possible. After the sliders 9 have reached said dismountable position, the bayonet coupling between the sliders 9 and the actuation device 7, 8 can be easily released, and the sliders 9 with the surgical instrument 5 mounted thereon can be completely removed from the shaft 3. This is shown in FIG. 8.

Figure 8:
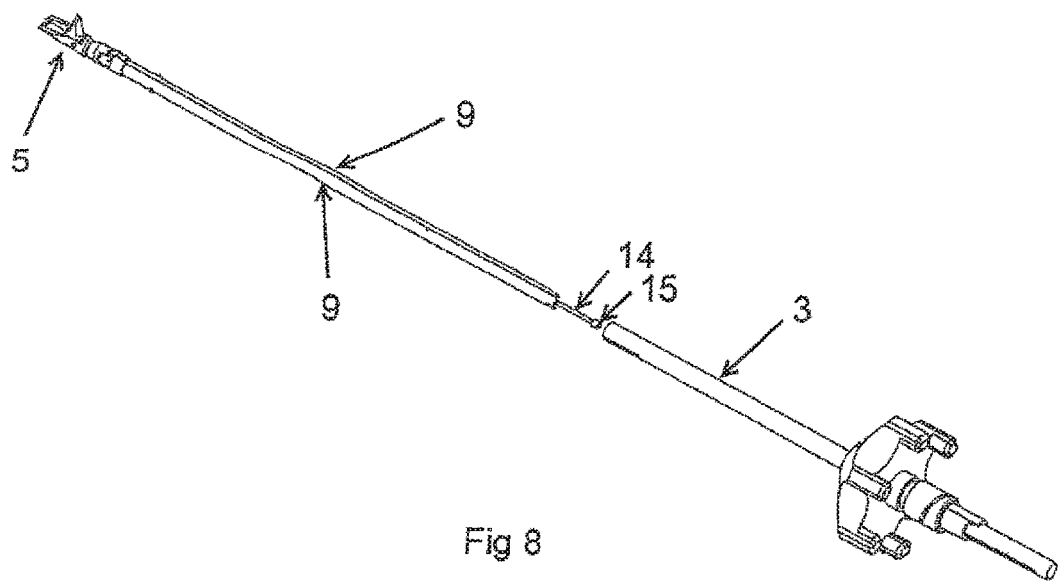
FIG. 8 shows the surgical device of the invention in some of its component parts.

FIG. 8 provides a further clear view on the feature that between the sliders 9 a central rod 14 is provided. This rod 14 has a fixed link with the surgical instrument 5, and has at its extremity distant from the surgical instrument 5 first locking means 15 that are arranged to cooperate with second locking means 16 as shown in FIG. 2 provided on the handgrip and/or mechanical actuation means. Preferably movement of the locking plate 11 from the first position to the second position is linked to releasing the first 15 and the second 16 locking means from each other.

Although the invention has been discussed in the foregoing with reference to an exemplary embodiment of the surgical device of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

What is claimed is:

1. Surgical device having a shaft with a distal end equipped with a surgical instrument, and a proximal end equipped with an actuation device for the surgical instrument, and wherein the surgical instrument is mounted on sliders that are longitudinally movable in opposite directions with respect to each other in the said shaft by operation of the said actuation device for actuating the surgical instrument, which sliders are provided adjacent to each other within said shaft, wherein said sliders comprise a first mounted position and a second dismountable position, wherein in the first mounted position the sliders are coupled with the actuation device and are secured while in this first mounted position against rotation within the said shaft, and wherein in the second dismountable position the sliders are concurrently slidable at least partly out of said shaft to a point at which rotation of the remainder of the sliders within the said shaft is enabled, and the actuation device is releasable, characterized in that the actuation device comprises an actuation wheel for the sliders mounted around and at the proximal end of the shaft, which actuation wheel is coupled to the sliders to convert rotational motion of said actuation wheel into longitudinal yet opposite motions of the sliders, and that a locking plate is provided which is movable between a first position in which it restricts movement of the actuation wheel along the shaft in its longitudinal direction, and a second position in which it enables movement of the actuation wheel along the shaft in its longitudinal direction, and that slits in said actuation wheel cooperate with radially outwards extending first pins mounted on longitudinally movable inserts that are further equipped with radially inwards extending second pins that reach through longitudinally provided slits in the shaft and eventually into apertures provided in the sliders within said shaft.

2. Surgical device according to claim 1, characterized in that the sliders are provided with sidewardly extending pins and the shaft is at its distal end provided with fissures or vice versa, wherein the sidewardly extending pins cooperate with the fissures to secure the sliders against rotation within the shaft.

3. Surgical device according to claim 2, characterized in that in the first position the locking plate secures the sliders in the first mounted position, and in the second position the locking plate secures the sliders in the second dismountable position.

4. Surgical device according to claim 2, characterized in that between the sliders a central rod is provided that has a fixed link with the surgical instrument, and which has at its extremity distant from the surgical instrument a first locking portion that is arranged to cooperate with a second locking portion provided on a handgrip and/or mechanical actuator.

5. Surgical device according to claim 4, characterized in that movement of the locking plate from the first position to the second position is linked to releasing the first locking portion and the second locking portion from each other.

6. Surgical device according to claim 1, characterized in that in said first position the locking plate secures the sliders in the first mounted position, and in the second position the locking plate secures the sliders in the second dismountable position.

7. Surgical device according to claim 6, characterized in that between the sliders a central rod is provided that has a fixed link with the surgical instrument, and which has at its extremity distant from the surgical instrument a first locking portion that are arranged to cooperate with a second locking portion provided on a handgrip and/or mechanical actuator.

8. Surgical device according to claim 7, characterized in that movement of the locking plate from the first position to the second position is linked to releasing the first locking portion and the second locking portion from each other.

9. Surgical device according to claim 1, characterized in that between the sliders a central rod is provided that has a fixed link with the surgical instrument, and which has at its extremity distant from the surgical instrument a first locking portion that is arranged to cooperate with a second locking portion provided on a handgrip and/or mechanical actuator.

10. Surgical device according to claim 9, characterized in that movement of the locking plate from the first position to the second position is linked to releasing the first locking portion and the second locking portion from each other.

11. Surgical device according to claim 1, wherein said surgical instrument is a grasper.

12. Surgical device according to claim 1, wherein said surgical device is sized and shaped for minimally invasive surgery.

13. Surgical device according to claim 1, wherein in the first mounted position said sliders are coupled through a bayonet coupling with the actuation device, to prevent releasing of the bayonet coupling between the sliders and the actuation device,
  wherein in the second dismountable position the bayonet coupling between the sliders and the actuation device is releasable, and
  wherein radially inwards extending second pins together with apertures in the sliders embody said bayonet coupling between the actuation device and the sliders.

* * * * *